United States Patent [19]
Tovey

[11] Patent Number: 5,333,624
[45] Date of Patent: Aug. 2, 1994

[54] SURGICAL ATTACHING APPARATUS

[75] Inventor: H. Jonathan Tovey, Milford, Conn.

[73] Assignee: United States Surgical Corporation, Norwalk, Conn.

[21] Appl. No.: 840,455

[22] Filed: Feb. 24, 1992

[51] Int. Cl.[5] ............................................. A61B 19/00
[52] U.S. Cl. ................................... 128/897; 600/37; 606/151
[58] Field of Search ............... 128/897–899; 600/37; 606/151–157, 222–226; 623/11, 12

[56] References Cited

U.S. PATENT DOCUMENTS

| | | |
|---|---|---|
| 460,940 | 10/1991 | Baugh . |
| 736,744 | 8/1903 | Kratzmueller . |
| 870,021 | 11/1907 | Duffee . |
| 2,092,929 | 9/1937 | Ovington ............................ 606/222 |
| 2,767,703 | 10/1956 | Wieburgs . |
| 3,525,339 | 8/1970 | Halligan . |
| 3,540,431 | 11/1970 | Mobin-Uddin . |
| 3,811,446 | 5/1974 | Lerwick et al. . |
| 3,840,015 | 10/1974 | Gain ................................... 606/222 |
| 4,041,931 | 8/1977 | Elliott et al. ....................... 606/151 |
| 4,190,042 | 2/1980 | Sinnreich . |
| 4,425,908 | 1/1984 | Simon . |
| 4,557,255 | 12/1985 | Goodman . |
| 4,586,502 | 5/1986 | Bedi et al. . |
| 4,732,150 | 3/1988 | Keener Jr. . |
| 4,807,626 | 2/1989 | McGirr . |
| 4,832,055 | 5/1989 | Palestrant . |
| 4,873,975 | 10/1989 | Walsh et al. ....................... 606/153 |
| 4,917,089 | 4/1990 | Sideris . |
| 4,955,889 | 9/1990 | Van Gent . |
| 5,053,047 | 10/1991 | Yoon ................................... 606/223 |
| 5,064,435 | 11/1991 | Porter . |
| 5,080,088 | 1/1992 | LeVahn . |
| 5,122,155 | 6/1992 | Eberbach ............................ 606/151 |
| 5,141,515 | 8/1992 | Eberbach ............................ 606/151 |
| 5,147,374 | 9/1992 | Fernandez .......................... 606/151 |
| 5,176,692 | 1/1993 | Wilk et al. .......................... 606/151 |

FOREIGN PATENT DOCUMENTS

| | | |
|---|---|---|
| 2567405 | 7/1984 | France . |
| 2071751 | 9/1981 | United Kingdom ............... 606/151 |

OTHER PUBLICATIONS

Surgical Laparoscopy & Endoscopy vol. 1, No. 3, pp.151-155, Raven Press, Ltd. (1991).

Primary Examiner—Lee S. Cohen
Assistant Examiner—John P. Lacyk

[57] ABSTRACT

An apparatus is disclosed for engaging surgical implants to facilitate the endoscopic application of the plant in laparoscopic surgery. The apparatus includes an attachment portion having an aperture therein and an anchor portion attached thereto. The invention also provides a method and apparatus for positioning surgical implants adjacent to body tissue.

62 Claims, 5 Drawing Sheets

SURGICAL ATTACHING APPARATUS

BACKGROUND OF THE INVENTION

1. Field of the Invention

The present invention relates to an apparatus and method for positioning surgical implants adjacent to body tissue to facilitate the fastening of the implant to the body tissue. More particularly, this invention relates to a cleat adapted for securing a surgical implant to a delivery device and for positioning the implant adjacent to body tissue.

2. Description of the Related Art

Hernias are abnormal protrusions of an organ or other body structure through a defect or natural opening in a covering membrane, muscle or bone. An inguinal hernia is a protrusion which makes its way through the abdomen in the inguinal (groin) region. Hernias may be divided into three general classes: direct inguinal hernia, indirect inguinal hernia and femoral hernia. In both a direct and indirect inguinal hernias, a part of the intestine may protrude through a defect (opening or tear) in the supporting abdominal wall to form a hernial sac. In a femoral hernia, a portion of the intestine is forced through the femoral ring into the femoral canal forming a hernial sac.

Hernia repair typically requires surgery which generally includes an incision in the groin ranging up to six inches in length. Several layers of the abdominal wall are generally separated to reach the herniated portions. During the procedure, the opening or tear in the abdominal wall is closed in a manner which resembles the tying of a sack at the neck. Often a surgical mesh is attached by sutures directly over the repaired hernia opening to provide a reinforcement to the opening.

Traditionally, such hernia repairs involved major invasive surgical procedures which often caused excessive trauma to the patient and necessitated unusually long post-operative recuperative periods. In addition, numerous complications, related directly or indirectly to the surgery often resulted, including bleeding, infection, testicular atrophy, organ damage, nerve damage, blood vessel damage, etc. Further, cutting through the numerous layers of tissue to obtain access to the herniated area often caused severe trauma to the patient. A detailed discussion of traditional hernia repair may be found in "Hernia Repair Without Disability, Second Edition", by Irving L. Lichtenstein. Such invasive surgical procedures have also been utilized in other areas of the body, including surgery on the gall bladder, appendix, lungs and the like.

To avoid many of the previously stated risks and problems, the use of laparoscopic and endoscopic surgical procedures have been relatively popular and has provided additional incentive to develop the procedures further. In laparoscopic procedures, surgery is performed in the interior of the abdomen through a small incision. Similarly, in endoscopic procedures, surgery is performed in any hollow viscus of the body through narrow endoscopic tubes inserted through small entrance wounds in the skin.

Laparoscopic and endoscopic procedures generally require that the surgical region be insufflated. Accordingly, any instrumentation inserted into the body must be sealed to ensure that gases do not enter or exit the body through the incision. Moreover, laparoscopic and endoscopic procedures often require the surgeon to act on organs, tissues and/or vessels far removed from the incision. Thus, instruments used in such procedures are typically long and narrow while being functionally controllable from a proximal end of the instrument.

In hernia surgery, as compared to gall bladder surgery, certain procedures and instruments are the same, and certain instrument requirements differ. For example, in hernia surgery a suitable mesh material is generally sutured over the opening in the tissue. Often, the mesh material is attached by sutures and left within the body to act as a reinforcing agent for tissue regrowth in the area of the surgery. One example of a mesh material currently utilized in hernia surgery includes a polypropylene material marketed by C. R. Bard, under the trademark MARLEX. Another example of a mesh material is a tri-fluoroethylene material marketed by W. L. Gore & Associates, Newark, Del., under the trademark GORE-TEX.

As noted, during conventional invasive surgical procedures, such mesh materials are manually placed over the defect in the abdominal wall and are often sutured within the surgical opening by conventional suturing techniques. However, with the advent of laparoscopic surgery the need for suitable mesh, mesh positioning and mesh attachment techniques through the relatively narrow endoscopic tubes or cannulas is clearly defined. Up to the present, such devices and techniques for mesh positioning have not yet been developed.

Heretofore, resilient umbrella type devices or extractors have been provided to remove objects from body tissue. Exemplary of these devices is U.S. Pat. No. 4,557,255 to Goodman. Goodman discloses a purse-like surgical net which is operable for retrieving stones and the like from within the human body.

U.S. Pat. No. 4,190,042 to Sinnreich discloses a resilient surgical retractor which in an unstressed condition forms a hook-like appendage at the distal end of the retractor.

U.S. Pat. No. 4,586,502 to Bedi et al. discloses a surgical instrument for implanting an "H"-shaped fastener in body tissue and a method of applying fasteners to skin or other tissue in a surgical procedure as an alternative to suturing a wound or surgical incision.

However, there remains a need for an apparatus which facilitates the securing of surgical implants for endoscopic positioning of the implant adjacent to body tissue. In addition to the above apparatus, the present invention relates to a method for positioning surgical implants adjacent to body tissue for stapling.

SUMMARY OF THE INVENTION

The present invention relates to surgical attaching apparatus for engaging surgical implants thereby facilitating attachment of the surgical implant to another structure such as an implant delivery device. The surgical attaching apparatus comprises an anchor means for engaging a surgical implant and an attachment means connected to the anchor means for receiving a suture or other securing device. In a particularly useful embodiment, the surgical attaching apparatus provides a cleat which receives a suture or other securing means for releasably attaching an implant to an implant delivery device. Preferably the surgical attaching apparatus is fabricated from material which is absorbable in body tissue, thereby eliminating the necessity for removing the apparatus from the surgical implant after deployment thereof adjacent to the body tissue. Alternatively, the surgical attaching apparatus can be fabricated from material which is non-absorbable in body tissue.

Further, a method is disclosed for positioning surgical implants adjacent to body tissue which comprises affixing at least one cleat to a surgical implant, affixing the surgical implant to a delivery device by passing a securing device through the cleat, positioning the surgical implant and delivery device adjacent to the body tissue, and releasing the surgical implant from the delivery device by removing the securing device from the cleat.

BRIEF DESCRIPTION OF THE DRAWINGS

Preferred embodiments of the invention are described hereinbelow with reference to the drawings wherein.

DETAILED DESCRIPTION OF THE PREFERRED EMBODIMENTS

Figures 1, 2:
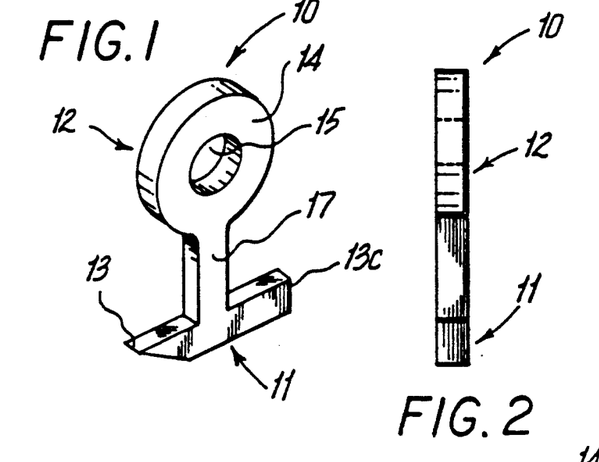
FIG. 1 is a perspective view of an apparatus of the present invention constructed for engaging surgical implants.
FIG. 2 is a side view of the apparatus in FIG. 1.

Referring now to the Figures and, in particular to FIGS. 1 and 2, a surgical attaching apparatus or cleat of the present invention is shown and generally indicated by the numeral 10, and includes an attachment portion 12 having an aperture 15 therein and an anchor portion 11 which is connected to the attachment portion 12. The anchor portion 11 is preferably elongated and may include one end 13 which is tapered or pointed, as shown in FIG. 1, enabling the cleat to be easily inserted into a surgical implant such as surgical mesh. Although the surgical implant will be discussed as a surgical mesh, the surgical implant may be embodied in a wide variety of configurations. The use of the term "surgical mesh" or "mesh" is not intended to limit the types of implants which may be used in the present invention. Whether one or more ends of the anchor portion of the cleat should be tapered will depend upon the tightness of the mesh or nature of the implant. The anchor portion may also have multiple arms, forming a cross or star-like structure or may even be disc-shaped. The anchor portion 11 may be any shape provided at least one portion thereof is adapted to engage the implant such as for example by insertion of the anchor portion at least partially through or into the implant.

Figure 3:
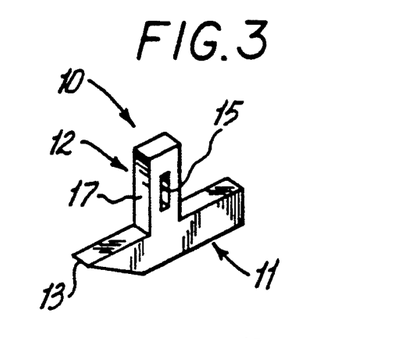
FIG. 3 is a perspective view of an alternate embodiment of the apparatus of the present invention.
Figure 4:
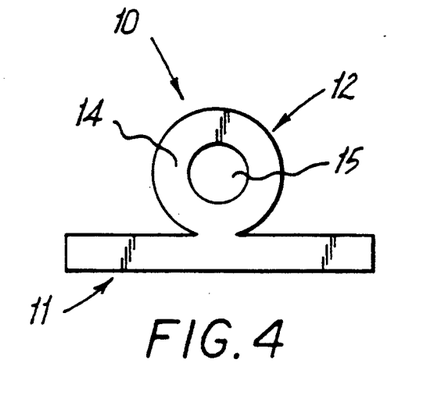
FIG. 4 is a side view of another alternate embodiment of the apparatus of the present invention.
Figure 5:
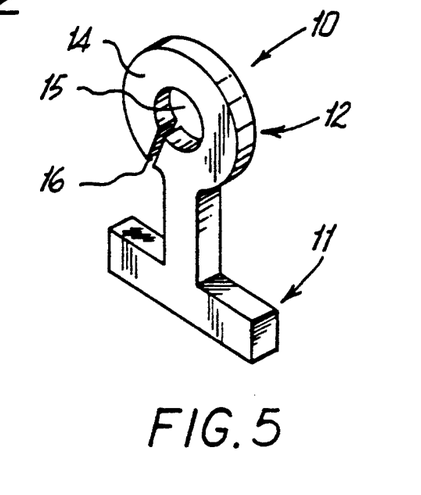
FIG. 5 is a perspective view of another alternate embodiment of an apparatus of the present invention.

The attachment portion 12 may include an upright portion 17. The aperture 15 may be formed directly in the upright portion 17 as shown in FIG. 3. Alternatively, the attachment portion 12 may include an eyelet 14. The eyelet 14 may be formed either on the upright portion 17 as shown in FIG. 1 or connected to the anchor portion 11 as shown in FIG. 4. Eyelet 14 may have a channel or opening 16 from the outer wall of the attachment portion 12 through to the aperture 15 as shown in FIG. 5 so that the suture or other securing device can be easily slipped into the aperture. Alternatively, the aperture may be completely enclosed as in FIGS. 1 and 4 requiring that the suture or other securing device be threaded therethrough. The aperture may be of any shape or form provided it adequately retains the suture or other securing means to facilitate the securing of the surgical mesh to another structure or device.

Preferably, the cleat is fabricated from materials which are absorbable in body tissue. Such absorbable materials include polymers and polymer blends derived at least in part from such monomers as glycolic acid, glycolide, lactic acid, lactide, p-dioxanone, trimethylene carbonate, e-caprolactone, hydroxycaproic acid, etc., and various combinations of these related monomers as disclosed, e.g., in U.S. Pat. Nos. 2,668,162; 2,703,316; 2,758,987; 3,225,766; 3,297,033; 3,422,181; 3,531,561; 3,565,077; 3,565,869; 3,620,218; 3,626,948; 3,636,956; 3,736,646; 3,772,420; 3,773,919; 3,792,010; 3,797,499; 3,839,297; 3,867,190; 3,878,284; 3,982,543; 4,047,533; 4,052,988; 4,060,089; 4,137,921; 4,157,437; 4,234,775; 4,237,920; 4,300,565; 4,429,080; 4,441,496; 4,523,591; 4,546,152; 4,559,945; 4,643,191; 4,646,741; 4,653,497; and 4,741,337; U.K. Patent No. 779,291; D. K. Gilding et al., "Biodegradable polymers for use in surgery—polyglycolide/poly(lactic acid) homo- and copolymers 1, *Polymer*, Volume 20, pages 1459–1464 (1979), and D. F. Williams (ed.), *Biocompatibility of Clinical Implant Materials*, Vol. II, ch. 9: "Biodegradable Polymers" (1981).

However, non-absorbable materials may also be used to fabricate the cleat. Such non-absorbable materials include the sparingly crosslinked poly(hydroxyethyl methacrylate) hydrogels disclosed in U.S. Pat. Nos. 2,976,576 and 3,220,960; hydrogels based on crosslinked polymers of n-vinyl lactams and alkyl acrylates as disclosed in U.S. Pat. No. 3,532,679; graft copolymers of hyroxyalkyl methacrylate and polyvinylpyrrolidone disclosed in U.S. Pat. No. 3,621,079. Other non-absorbable materials include stainless steel and titanium. The above named non-absorbable materials are only exemplary, other inert metals and plastics that do not react with body tissue which may come to the mind of those skilled in the art are also contemplated.

The method for positioning surgical implants adjacent to body tissue includes affixing at least one cleat to a surgical mesh, affixing the surgical mesh to a delivery device by passing a securing device through the cleat, positioning the surgical mesh and delivery device adjacent to the body tissue, and releasing the surgical mesh from the delivery device by removing the securing device from the cleat. The number of cleats required will depend upon the shape, weight, and composition of the implant, the configuration of the delivery device and the precision with which the implant must be maneuvered by the delivery device or otherwise.

Figure 6:
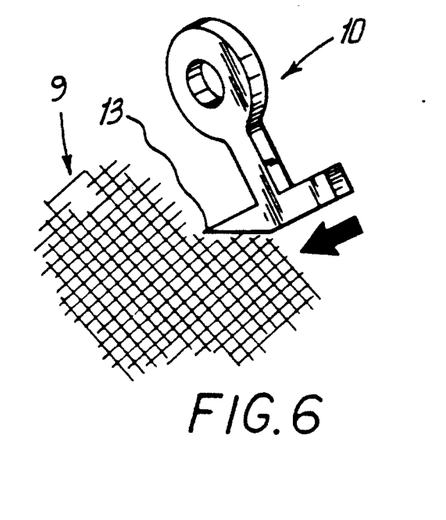
FIG. 6 is a perspective view illustrating the insertion of the apparatus of the present invention into a mesh surgical implant.
Figure 7:
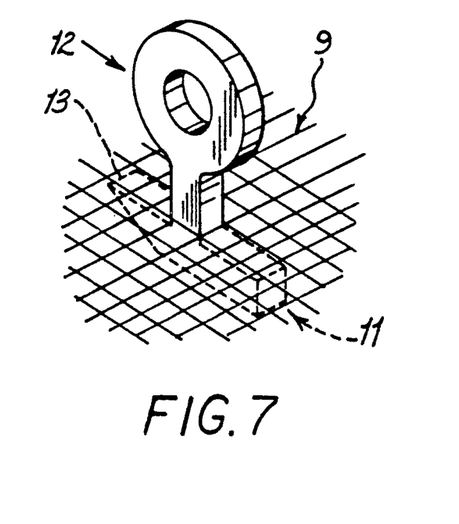
FIG. 7 is a perspective view illustrating the apparatus of the present invention fully engaged with the mesh surgical implant.

Affixing the cleat to the surgical mesh may be accomplished by inserting tapered portion 13 at least partially through the mesh. As best illustrated in FIG. 6 and FIG. 7, and utilizing the preferred anchor portion shown in FIG. 1, cleat 10 is tilted to insert tapered end 13 through the surgical mesh such that the anchor portion is on one side of the mesh and the attachment portion is on the other side of the mesh. Depending on the structure or composition of the implant, the anchor portion may need to only partially penetrate the implant, such as, for example, where the implant is made up of more than one layer of material, or where the implant includes a skin. As other examples, where the implant comprises a sponge-like or gel-like material the cleat need not be placed through the entire thickness of the implant to sufficiently engage the implant. The only requirement is that the anchor portion sufficiently engage the implant in a manner which allows access to the attachment portion of the cleat.

Figure 8:
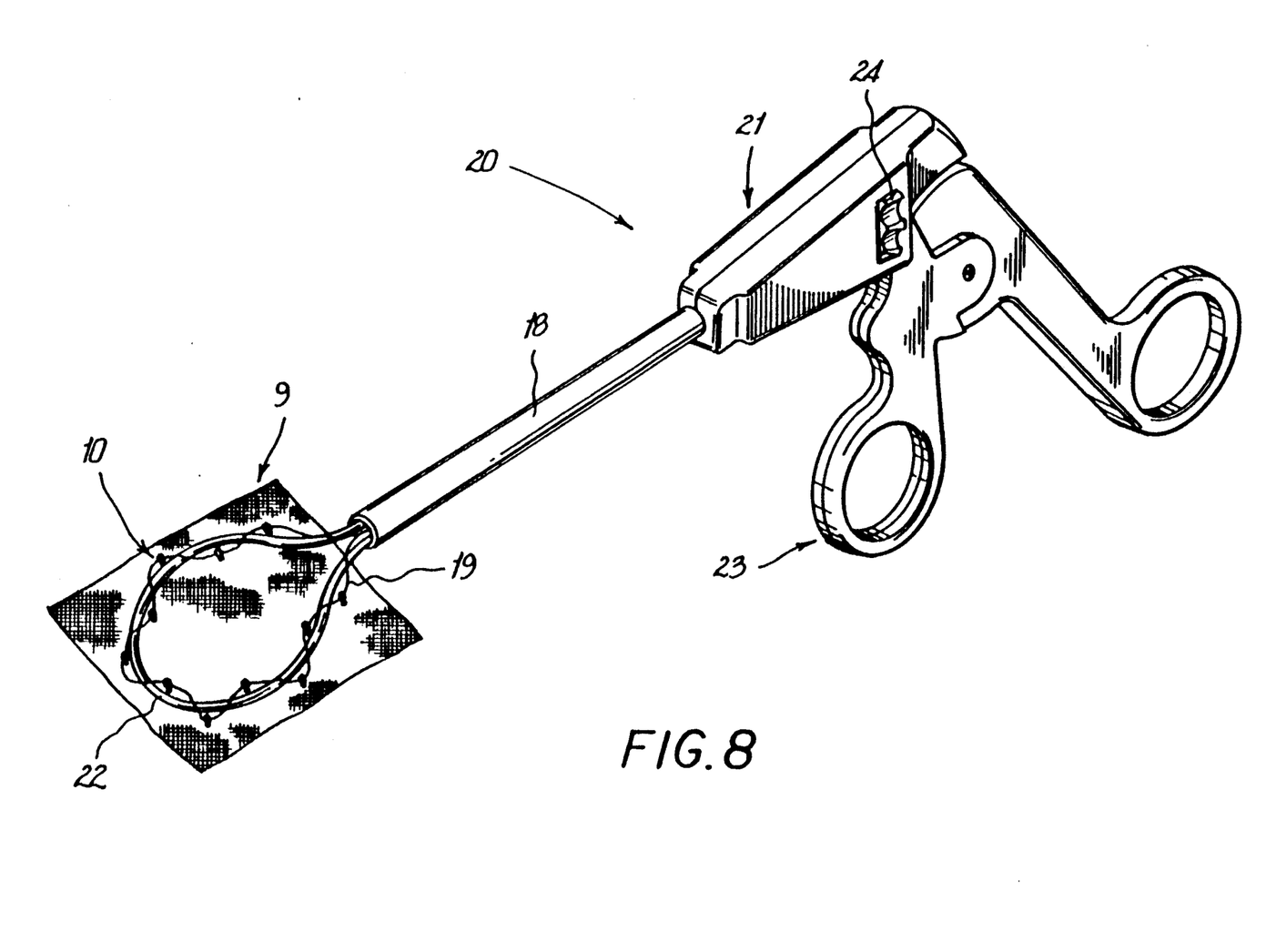
FIG. 8 is a perspective view of an endoscopic implant delivery device having a surgical implant secured thereto by the apparatus of the present invention.
Figure 9:
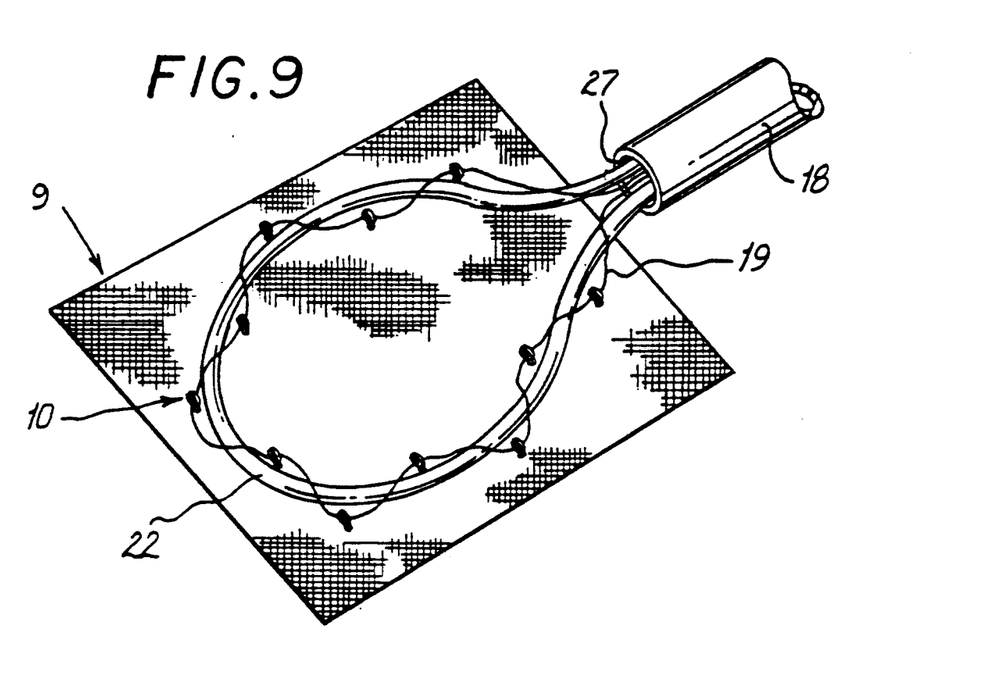
FIG. 9 is a perspective view of the distal end of the endoscopic implant delivery device with the surgical implant deployed and affixed thereto.

The surgical mesh is affixed to a delivery device using a suture or other securing device. Preferably, a suture 19 may simply be passed through each cleat, without wrapping around the delivery device, such that the delivery device 20 is positioned between the suture 19 and the surgical mesh 9 as shown in FIG. 8. Alternatively, a suture 19 may be passed through the cleats 10, while between the cleats the suture 19 is wrapped around the delivery device 20 as shown in FIG. 9. In another embodiment the surgical mesh is affixed to the delivery device by passing a suture 19 through an individual cleat 10 and tying the suture around the delivery device 20, repeating the this technique for each cleat that is affixed to the surgical mesh or for a sufficient number of cleats so as to adequately secure the surgical mesh to the delivery device for the particular application of the implant.

While described as a suture, it should be understood that other types of yarns, threads, fibers or filaments may be used as the securing device. In addition, the securing device may be any flexible or rigid member for securing the cleat to the delivery device. Preferably, the securing device is constructed to allow removal thereof to facilitate release of the implant from the delivery device.

Figure 10:
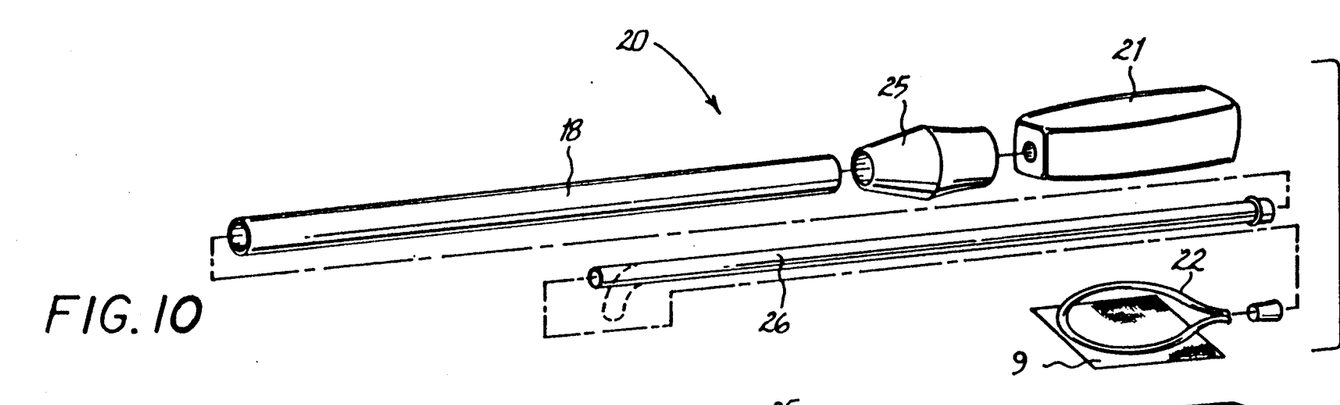
FIG. 10 is an exploded view of the preferred endoscopic implant delivery device having a reciprocating tubular sheath.

The delivery device 20 generally includes a support member 22 which preferably forms an elongated structure at its proximal end or is located at the end of an elongated rod 26 shown in FIG. 10. The configuration of the support member 22 is adapted to facilitate securing of the implant thereto via the cleats of the present invention and allow manipulation of the implant. For example, the support member may be frame-like, forming a circular, oval, square, triangular, polyhedral or irregular-shaped frame. As another example, the support member may be "T", "H" or "Y" shaped. As yet another example, the support member may be solid in form and assist in pressing the implant against the body tissue. The support member may also be provided with eyelets through which the suture or other securing device passes after passing through one or more cleats.

Figures 11, 12:
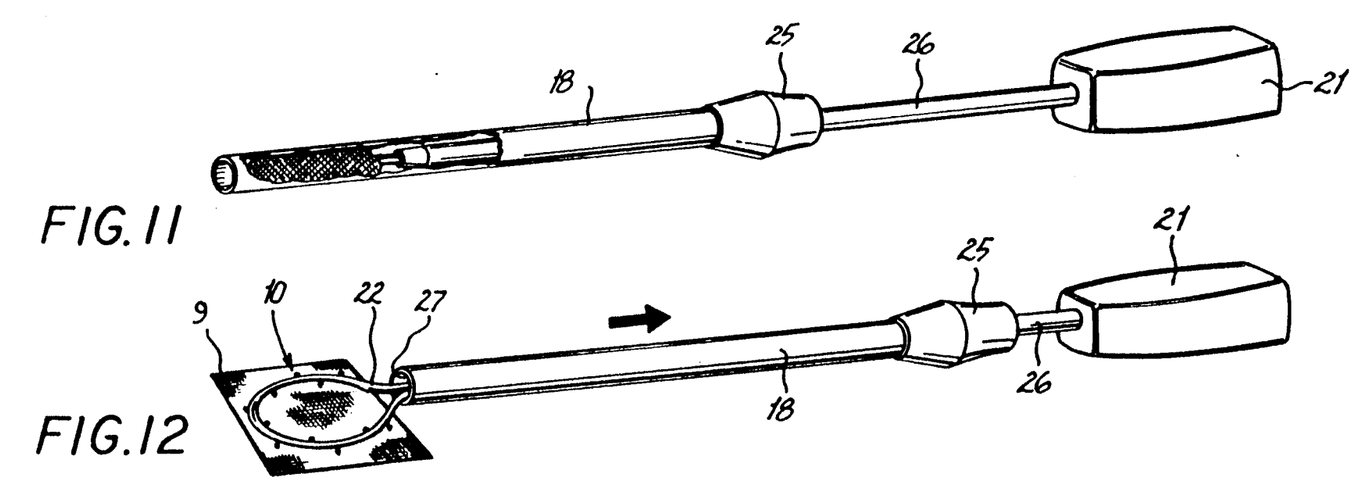
FIG. 11 is a perspective view of the preferred endoscopic implant delivery device illustrating a reciprocating tubular housing member having a surgical implant secured to a delivery device and retained therein.
FIG. 12 is a perspective view of the preferred endoscopic implant delivery device of FIG. 11 illustrating a reciprocating tubular housing member having a surgical implant secured to a delivery device and extended therefrom.

Once the implant is affixed to the delivery device, the surgical mesh and delivery device are positioned adjacent to the body tissue. The surgical mesh and delivery device may be positioned adjacent to the body tissue manually during conventional invasive surgical procedures. Preferably, however, for use with a hernia repair mesh, the delivery device is an endoscopic instrument which includes a support member 22 located at the distal end of an elongated rod 26. The elongated rod 26 extends through an elongated tubular housing member comprising the endoscopic portion 18 of the instrument and is connected at a proximal end to a handle assembly 21 as shown in FIG. 10. The endoscopic portion 18 of the instrument reciprocates along the longitudinal axis of the rod 26 so as to retain and extend the surgical mesh, as shown in FIGS. 11 and 12. In a preferred embodiment, the proximal end of the endoscopic portion 18 has a gripping means 25 secured thereto, which facilitates the reciprocating movement of the endoscopic portion 18 along the longitudinal axis of the elongated rod 26. As an illustration, the surgeon may reciprocate the endoscopic portion 18 by holding the gripping means 25 in one hand and the handle portion 21 in the other and sliding the endoscopic portion 18 along the rod 26 causing the support member 22 to extend from or retract into the endoscopic portion 18.

The gripping means may be in the form of a substantially conically shaped knob 25 as shown in FIG. 10. However, the gripping means may be configured in any form so long as it facilitates the reciprocal movement of the endoscopic portion 18 along the longitudinal axis of the elongated rod 26. For example, the gripping means may be barrel, disk or mushroom shaped member, as well as any other irregular shaped member. Additionally, a grip enhancing means may be formed on or attached to the gripping means, which allows the surgeon to firmly grasp the gripping means. The grip enhancing means may be in the form of protrusions extending from the gripping means or knurling formed on the gripping means.

In an alternate embodiment, the rod 26 may extend through the endoscopic portion 18, which is connected to the handle assembly 21, and operatively connected at the proximal end to the handle assembly 21, as illustrated in FIG. 8. Actuation of the handle assembly 21, by trigger means 23, selectively causes longitudinal distal movement of the rod 26 causing the support member 22 to extend out of the endoscopic portion 18 of the instrument.

In still another embodiment, the elongated rod 13 may extend through the endoscopic portion 18 and reciprocate within the endoscopic portion 18 so as to retain and extend the surgical mesh. The proximal end of the rod has a handle assembly (not shown) connected thereto and the proximal end of the endoscopic portion has finger gripping means (not shown) secured thereto. This configuration allows the surgeon to apply pressure to the handle assembly along the rod's longitudinal axis with at least one finger and to firmly grasp the finger gripping means with the remaining fingers, thereby causing the elongated rod to reciprocate within the endoscopic portion. The finger gripping means may be arcuate, straight, circular or elliptical members which allow the surgeon to grasp the members with his or her fingers.

Generally, the handle portion 21 may be configured in any shape or form which can be manipulated during surgery. The handle portion 21 may further include a rotation means 24, allowing the surgeon to rotate the support member 22 when positioning the implant, as shown in FIG. 8.

Figures 13, 14, 15:
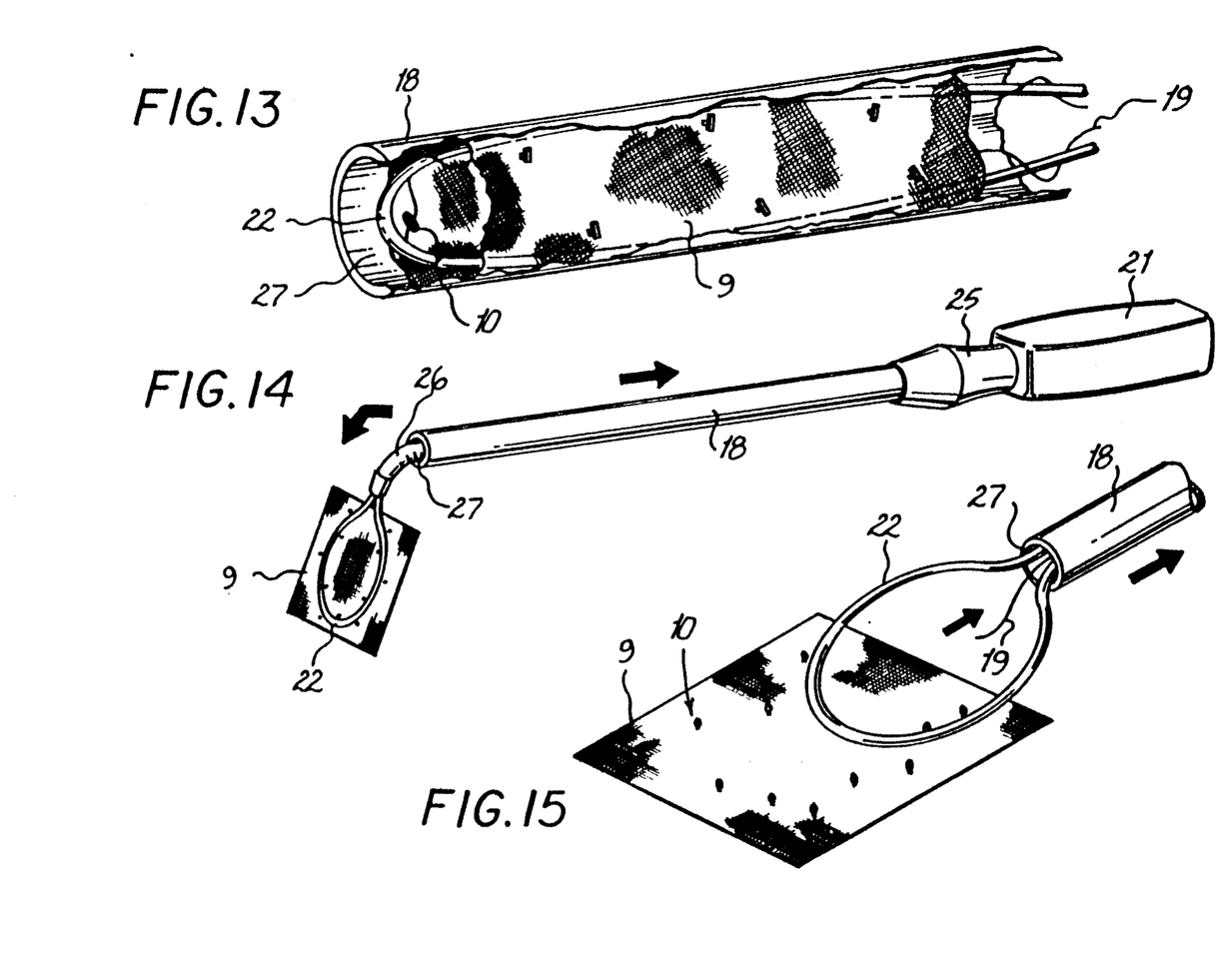
FIG. 13 is a perspective view in partial cut away of the distal end of the endoscopic implant delivery device of FIG. 11.
FIG. 14 is a perspective view of the endoscopic implant delivery device of FIG. 11 with the surgical implant deployed and affixed to a delivery device fabricated from an elastic material.
FIG. 15 is a perspective view illustrating the retraction of the securing device and implant delivery device after release of the surgical implant.

The support member 22 of the delivery device is preferably fabricated from an elastic material that displays flexible, resilient memory properties. As shown in FIGS. 11 and 13 the use of elastic materials allows the surgical mesh 9 and support member 22 to be compressed and retracted into an endoscopic portion 18 of the instrument. The elastic nature of the material will allow the support member 22 and surgical mesh 9 to return to their original configuration when extended out of the endoscopic portion 18 of the instrument.

In a preferred embodiment, the distal end of rod 26 is fabricated from an elastic material which, in its unstressed state, assumes an angle with respect to the longitudinal axis of the endoscopic portion 18 of the instrument, as shown in FIG. 14. When the rod 26 is retracted into the tube of the endoscopic instrument, it cams against the distal end 27 of the tube and assumes a relatively straightened configuration within the tube. When the elastic portion of the rod 26 begins to extend beyond the distal end 27 of the tube of the endoscopic portion 18 the elastic nature of this portion of the rod causes the rod to begin to bend, as shown by the arrow, changing the orientation of the support member 22 and implant with respect to the endoscopic portion 18 of the instrument.

As a greater portion or the elastic portion of the rod 26 extends further beyond the distal end 27 of the tube, the angular orientation of the support member 22 becomes greater. Ultimately, the rod 26 may extend out of the distal end 27 of the tube a distance sufficient to fully remove the stress from rod 26, whereupon the elastic material returns to its unstressed configuration, providing the maximum angle with respect to the longitudinal axis of the endoscopic portion 18 of the instrument.

Employing an elastic material at the distal end of rod 26 allows delivery of the surgical mesh at a desired orientation or pressing of the mesh against the body tissue making it easier for the surgeon to fasten the surgical mesh to the tissue. It also enables the surgeon to position the delivery device and surgical mesh in areas where a straight device would be difficult or inconvenient to use.

Elastic materials contemplated for fabricating the support member and or the distal portion of the rod are those that have spring-like properties such that they are capable of being deformed by an applied stress and then return, or recover, to their original shape or configuration when the stress is removed. The elastic material can be either polymeric or metallic or a combination thereof, however, it is preferred that it be highly elastic. For example, such elastic materials may include silicone, polyvinyl resins, polyethylene, resilient polyacetals, polyurethane, resilient polycetals, polyurethane, synthetic rubbers, teflon, tetrafluorethylene fluorocarbon polymer, spring-tempered steel, and spring tempered stainless steel.

In addition, shape memory alloys may be used for the elastic material. Shape-memory alloys which exhibit pseudoelastic or superelastic properties are preferred. Fundamentally, alloys which are capable of transforming between martensitic and austenitic shapes are able to exhibit shape-memory effect. The transformation between the martensitic and austenitic phases may be caused by temperature or stress.

In the case of pseudoelastic shape memory alloys, conditions may occur where temperature is not relied on to accomplish shape change. Further, pseudoelastic alloys may be elastically deformed far beyond the elastic limits of conventional metals. Suitable shape memory alloys are described in U.S. Pat. No. 4,665,906.

Once in position the surgical mesh is released from the delivery device by removing the securing device from the cleat. In the preferred embodiment the securing device is a single suture or a plurality of sutures which are continuously threaded through the cleats as discussed above. The suture 19 is passed through each cleat 10 and extends into the endoscopic portion 18 of the instrument, as shown in FIG. 15, and either exits the instrument at the handle assembly 21 to allow manual removal of the suture or alternatively may be operatively connected to the handle assembly where a trigger or other actuating structure (not shown) causes withdrawal of the suture. Since the suture is merely threaded through the cleats the suture is easily pulled through the aperture 15 in the cleats, sequentially releasing the delivery device from each cleat. Alternatively, the surgeon may remove the suture 19 or securing device by manually cutting the suture or securing device using conventional cutting devices at one or more cleats as required to release the mesh from the delivery device. Once the securing device is removed, the mesh may be held in place by the delivery device pressing it against the body tissue. Alternatively, the mesh may be secured to the body tissue prior to removal of the securing device. The mesh may be secured in place to the body tissue by means of suture, clips and/or staples.

It will be understood that various modifications can be made to the embodiments of the present invention herein disclosed without departing from the spirit and scope thereof. For example, various sizes of the instrument are contemplated, as well as various types of construction materials. Also, various modifications may be made in the configuration of the parts. Therefore the above description should not be construed as limiting the invention but merely as exemplifications of preferred embodiments thereof. Those skilled in the art will envision other modifications within the scope and spirit of the present invention as defined by the claims appended hereto.

What is claimed is:

1. Surgical attaching apparatus comprising:
   anchor means adapted to engage a surgical implant; and
   attachment means attached to said anchor means having an aperture formed therein adapted to receive at least one securing device, said attachment means being attached to said anchor means so as to form a substantial "T" shape.

2. Surgical attaching apparatus according to claim 1 wherein said attachment means and said anchor means are fabricated from a bioabsorbable material.

3. Surgical attaching apparatus according to claim 1 wherein said anchor means includes a tapered portion.

4. Surgical attaching apparatus according to claim 1 wherein said anchor means includes a pointed portion.

5. A method for positioning surgical implants adjacent to body tissue, comprising:
   affixing at least one surgical attaching apparatus to a surgical implant;
   affixing said surgical implant to a delivery device by passing a securing device through said at least one surgical attaching apparatus;
   positioning said surgical implant and said delivery device adjacent to the body tissue; and
   releasing said surgical implant from said delivery device by removing said securing device from said at least one surgical attaching apparatus.

6. A method according to claim 5 wherein the step of affixing said surgical implant to said delivery device further comprises the step of passing a securing device through a plurality of said surgical attaching apparatus such that said delivery device is positioned between said securing device and said implant.

7. A method according to claim 5 wherein the step of affixing said surgical implant to said delivery device further comprises the step of passing a securing device through a plurality of said surgical attaching apparatus while between each of said surgical attaching apparatus the securing device is wrapped around said delivery device.

8. Apparatus for positioning surgical implants adjacent to body tissue, comprising:
   an elongated rod having a support member formed on a distal end thereof;
   a surgical implant adapted to be releasably attached to said support member;
   at least one surgical attaching apparatus attached to said surgical implant, said surgical attaching apparatus having an anchor means for engaging said surgical implant and attachment means connected to said anchor means, said attachment means having an aperture formed therein; and
   at least one securing device adapted to be received in said aperture of said surgical attaching apparatus for releasably securing said surgical implant to said support member.

9. Apparatus according to claim 8 wherein said attaching apparatus is fabricated from a bioabsorbable material.

10. Apparatus according to claim 8 wherein said surgical implant comprises a surgical mesh.

11. Apparatus according to claim 8 wherein said securing device comprises a suture.

12. Apparatus according to claim 8 wherein said support member is fabricated from elastic material.

13. Apparatus according to claim 12 wherein said elastic material is shape-memory alloy.

14. Apparatus according to claim 12 wherein said elastic material is a superelastic metallic alloy.

15. Apparatus according to claim 8 wherein said support member is shaped in the form of a closed loop.

16. Apparatus according to claim 8 wherein said elongated rod includes a portion which is fabricated from an elastic material at a distal end thereof.

17. Apparatus according to claim 16 wherein said elastic material has an unstressed configuration at an angle with respect to the longitudinal axis of a proximal end of said elongated rod.

18. Apparatus according to claim 16 wherein said elastic material is a shape-memory alloy.

19. Apparatus according to claim 16 wherein said elastic material is a superelastic metallic alloy.

20. Apparatus for positioning surgical implants adjacent to body tissue, comprising:
   an elongated tubular housing member;
   an elongated rod having a support member formed on a distal end thereof and a handle formed on a proximal end thereof, said elongated rod being disposed coaxially in said elongated tubular housing member and adapted for relative reciprocal motion to move said support member between a first extended position and a second retracted position;
   a surgical implant adapted to be releasably attached to said support member;
   at least one surgical attaching apparatus attached to said surgical implant, said surgical attaching apparatus having an anchor means for engaging said surgical implant and attachment means connected to said anchor means; and
   at least one securing device adapted to engage said attachment means so as to secure said surgical implant to said support member.

21. Apparatus according to claim 20 wherein said elongated tubular housing member further comprises a gripping means connected to a proximal end thereof.

22. Apparatus according to claim 21 wherein said gripping means comprises a substantially conically shaped knob.

23. Apparatus according to claim 21 wherein said gripping means includes a grip enhancing means on an outer surface thereof.

24. Apparatus according to claim 20 wherein said attaching apparatus is fabricated from a bioabsorbable material.

25. Apparatus according to claim 20 wherein said surgical implant comprises a surgical mesh.

26. Apparatus according to claim 20 wherein said securing device comprises a suture.

27. Apparatus according to claim 20 wherein said support member is fabricated from elastic material.

28. Apparatus according to claim 27 wherein said elastic material is shape-memory alloy.

29. Apparatus according to claim 27 wherein said elastic material is a superelastic metallic alloy.

30. Apparatus according to claim 20 wherein said support member is shaped in the form of a closed loop.

31. Apparatus according to claim 20 wherein said elongated rod includes a portion which is fabricated from an elastic material.

32. Apparatus according to claim 31 wherein said elastic material has an unstressed configuration at an angle with respect to the longitudinal axis of said elongated tubular housing member.

33. Apparatus according to claim 31 wherein said elastic material is a shape-memory alloy.

34. Apparatus according to claim 31 wherein said elastic material is a superelastic metallic alloy.

35. Apparatus for positioning surgical implants adjacent to body tissue, comprising:
   an elongated tubular housing member having a first handle portion attached to a proximal end thereof and a second handle portion associated with said housing member and pivotally connected to said first handle portion;
   an elongated rod having a support member formed on a distal end thereof, said elongated rod being disposed coaxially in said tubular housing member and operatively connected to said second handle portion for reciprocal movement of said support member between a first extended position and a second retracted position;

a surgical implant adapted to be releasably attached to said support member;

at least one surgical attaching apparatus attached to said surgical implant, said surgical attaching apparatus having an anchor means for engaging said surgical implant and attachment means connected to said anchor means; and at least one securing device adapted to engage said attachment means so as to secure said surgical implant to said support member.

36. Apparatus according to claim 35 further comprising rotation means for rotating said elongated rod about its longitudinal axis.

37. Apparatus according to claim 35 wherein said at least one surgical attaching apparatus is fabricated from a bioabsorbable material.

38. Apparatus according to claim 35 wherein said surgical implant comprises a surgical mesh.

39. Apparatus according to claim 35 wherein said securing device comprises a suture.

40. Apparatus according to claim 35 wherein said support member is fabricated from elastic material.

41. Apparatus according to claim 40 wherein said elastic material is shape-memory alloy.

42. Apparatus according to claim 40 wherein said material is a superelastic metallic alloy.

43. Apparatus according to claim 35 wherein said support member is shaped in the form of a closed loop.

44. Apparatus according to claim 35 wherein said elongated rod includes a portion which is fabricated from an elastic material.

45. Apparatus according to claim 44 wherein said elastic material has an unstressed configuration at an angle with respect to the longitudinal axis of said elongated tubular housing member.

46. Apparatus according to claim 44 wherein said elastic material is a shape-memory alloy.

47. Apparatus according to claim 44 wherein said elastic material is a superelastic metallic alloy.

48. Apparatus for positioning surgical implants adjacent to body tissue, comprising:

an elongated tubular housing member having an endoscopic portion formed at a distal end thereof;

an elongated rod having a support member formed on a distal end thereof and a handle formed on a proximal end thereof, said elongated rod being disposed coaxially in said elongated tubular housing member and adapted for relative reciprocal motion to move said support member between a first extended position and a second retracted position;

a surgical implant adapted to be releasably attached to said support member;

at least one surgical attaching apparatus attached to said surgical implant, said surgical attaching apparatus having an anchor means for engaging said surgical implant and attachment means connected to said anchor means; and at least one securing device adapted to engage said attachment means so as to secure said surgical implant to said support member.

49. Apparatus according to claim 48 wherein said elongated tubular housing member further comprises a gripping means connected to a proximal end thereof.

50. Apparatus according to claim 49 wherein said gripping means comprises a substantially conically shaped knob.

51. Apparatus according to claim 49 wherein said gripping means includes a grip enhancing means on an outer surface thereof.

52. Apparatus according to claim 48 wherein said attaching apparatus is fabricated from a bioabsorbable material.

53. Apparatus according to claim 48 wherein said surgical implant comprises a surgical mesh.

54. Apparatus according to claim 48 wherein said securing device comprises a suture.

55. Apparatus according to claim 48 wherein said support member is fabricated from elastic material.

56. Apparatus according to claim 55 wherein said elastic material is shape-memory alloy.

57. Apparatus according to claim 55 wherein said elastic material is a superelastic metallic alloy.

58. Apparatus according to claim 48 wherein said support member is shaped in the form of a closed loop.

59. Apparatus according to claim 48 wherein said elongated rod includes a portion which is fabricated from an elastic material.

60. Apparatus according to claim 59 wherein said elastic material has an unstressed configuration at an angle with respect to the longitudinal axis of said elongated tubular housing member.

61. Apparatus according to claim 59 wherein said elastic material is a shape-memory alloy.

62. Apparatus according to claim 59 wherein said elastic material is a superelastic metallic alloy.

* * * * *